United States Patent [19]

Sandine et al.

[11] Patent Number: 4,615,978
[45] Date of Patent: Oct. 7, 1986

[54] BACTERIAL GROWTH MEDIUM AND METHOD OF USE

[75] Inventors: William E. Sandine; James W. Ayres, both of Corvallis, Oreg.

[73] Assignee: The State of Oregon, by and through the Oregon State Board of Higher Education on behalf of Oregon State University, Eugene, Oreg.

[21] Appl. No.: 682,495

[22] Filed: Dec. 18, 1984

Related U.S. Application Data

[63] Continuation of Ser. No. 450,797, Dec. 17, 1982, abandoned, which is a continuation of Ser. No. 237,883, Feb. 25, 1981, abandoned, which is a continuation-in-part of Ser. No. 52,960, Jun. 28, 1979, Pat. No. 4,282,255.

[51] Int. Cl.$^4$ .................. C12N 1/20; C12P 7/56; A23C 9/123; A23C 9/12
[52] U.S. Cl. ................. 435/253; 435/139; 426/7; 426/34; 426/36; 426/42; 426/43
[58] Field of Search ............ 426/7, 34, 42, 43; 435/139–141, 144, 253

[56] References Cited

U.S. PATENT DOCUMENTS

3,410,755 11/1968 Etchells et al. .
4,163,692 8/1979 Yates ................................ 435/254

OTHER PUBLICATIONS

Bridson et al., "Design and Formulation of Microbial Culture Media", in Norris et al. (eds.), *Methods in Microbiology*, pp. 229–295 (1970).
Chen et al., "Lactic Bulk Culture System Utilizing Whey-Based Bacteriophage Inhibitory Medium and pH Control. III. Applicability to Cottage Cheese Manufacture", *J. Dairy Sci.*, 60:1252–1255 (1977).
Davis, *Cheese*, vol. I, 214, 215, 237, 238 (1965).
Doull et al., "Phage Suppression and the Cultivation of Lactic Streptococci" (abstract), *Proceedings*, 13th Int. Dairy Cong., 1:391 (1953).
Doull et al., "Phage Suppression and the Cultivation of Lactic Streptococci", *Proceedings*, 13th Int. Dairy Cong., 3:1114–1120 (1953).
Frei et al., "Starter Culture Media with Built—in Controls, Reduces Inoculum Costs, Improves Operating Efficiencies, Inhibits Phage, and Produces More Viable Cultures", *Food Processing* (Feb. 1980).
Jonas, "Major Savings Realized in the Production of Bulk Lactic Culture with Whey—based Phage Inhibitory Medium Provided with pH Control", *Cultured Dairy Products J.*, pp. 12–14 (May 1977).
Linke, *Solubilities*, vol. II, 520–524 (1965).
Odagiri et al., "Chain Length Determination of Polyphosphates", *J. Dairy Sci.*, 47:920–921 (1964).
Olson, "pH Control During Lactic Starter Production", *Dairy Field*, 92, 94 (1981).
Potter et al., "Effects of Calcium on Proliferation of Lactic Streptococcus Bacteriophage. II. Studies of Optimum Concentrations in a Partially Defined Medium", *J. Bact.*, 64:114–115 (1952).
Roundtree, "Staphylococcal Bacteriophages", *Australian J. Exper. Biol.*, 25:203–212 (1947).
Shew, "Effect of Calcium on the Development of Streptococcal Bacteriophages", *Nature*, 164:492–493 (1949).
Waksman, *Microbial Antagonism and Antibiotic Substances*, 64–69 (1947).
Willrett et al., "Evaluation of a New pH–Controlled Bulk Starter Medium", Paper presented at Wisconsin Cheesemakers Association. Meeting, Oct. 31, 1979.
505920-21, "Procedure for the Determination of Phage Titer", pp. 1–2.

*Primary Examiner*—Lionel M. Shapiro
*Attorney, Agent, or Firm*—Klarquist, Sparkman, Campbell, Leigh & Whinston

[57] ABSTRACT

An improved powdered bacterial growth medium composition adapted to be admixed with water is described. The powdered growth medium includes an alkaline earth metal cation in a compound A admixed with a compound B containing an anion which reacts with the alkaline earth metal cation in compound A in an aqueous growth medium to form an essentially water insoluble salt or base, including the alkaline earth metal cation and the anion, which is acid neutralizing. The water insoluble salt is thus formed in situ in the aqueous growth medium when compounds A and B are added to the aqueous solution. Also described is an improved method for growing acid producing bacteria in an aqueous growth medium by forming the insoluble salt or base. The resulting growth medium is particularly adapted for neutralizing acids generated during growth of lactic acid producing bacteria which are grown for use in various food fermentations.

14 Claims, No Drawings

BACTERIAL GROWTH MEDIUM AND METHOD OF USE

This application is a continuation of application Ser. No. 450,797, filed Dec. 17, 1982, now abandoned which is a continuation of application Ser. No. 237,883, filed Feb. 25, 1981, now abandoned, which is a continuation-in-part of application Ser. No. 52,960, filed June 28, 1979, now U.S. Pat. No. 4,282,255,

BACKGROUND OF THE INVENTION

1. Field of the Invention

The present invention relates to an improved method and compositions for growing acid producing bacteria wherein an essentially water insoluble alkaline earth metal salt or base is generated in situ in the aqueous growth medium. In particular, the present invention relates to the use of a powdered growth medium composition containing an alkaline earth metal cation and an anion which reacts to form the insoluble salt or base when the powder is added to an aqueous solution.

2. Prior Art and Related Patent Application

In our application Ser. No. 52,960, now U.S. Pat. No. 4,282,255 we described prior art relating to neutralization in growing acid producing bacteria. This earlier application particularly describes an improvement in the use of a water insoluble base or salt as a neutralizing agent for the acid generated by the bacteria. This method works extremely well; however, various considerations, particularly cost and availability of chemicals as discussed hereinafter, dictated finding a method wherein the insoluble neutralizing agent was prepared in a different manner. Also, the insoluble salts and bases may be granular rather than powdered or require hammer milling to prevent mixing problems both before and during use of the compositions which may limit their effectiveness.

The reaction of compounds in water to produce soluble or insoluble salts is well known in the general chemical literature. However, the inventors are not aware of any prior art which deals with the in situ generation of an insoluble neutralizing agent in a bacterial growth media.

OBJECTS

It is therefore an object of the present invention to provide a method wherein an insoluble alkaline earth metal salt or base as a neutralizing agent is generated in situ in an aqueous growth medium when selected compounds are added to the aqueous growth medium, wherein the resulting medium is very effective for growing acid producing bacteria. It is further an object of the present invention to provide a method to generate essentially water insoluble neutralizing agents in situ by chemical reaction of appropriate compounds in the aqueous growth medium, so as to maintain a pH which minimizes the adverse effects of acid produced during bacterial growth and therefore maximizes the number and fermentation activity of the cells. It is further an object of the present invention to provide a method and compositions which generate a well dispersed insoluble salt or base as a neutralizing agent in the aqueous growth medium. Further still, it is an object of the present invention to provide a method and compositions which are very economical and use readily available chemicals. These and other objects will become increasingly apparent by reference to the following description.

GENERAL DESCRIPTION

The present invention relates to an improvement in the method for growing acid producing bacteria in an aqueous growth medium including bacterial nutrients which comprises reacting in the aqueous growth medium a water soluble alkaline earth metal cation in a compound A with an anion in a compound B which reacts with the alkaline earth metal cation to form an essentially water insoluble salt, base or mixture thereof, including the alkaline earth metal cation and the anion, which is acid neutralizing in the medium, wherein the resulting medium is adapted to provide an amount of the insoluble salt or base or mixture thereof in the aqueous medium sufficient to neutralize at least some of the acid generated by the acid producing bacteria and wherein the resulting medium is non-toxic to the bacteria.

The present invention further relates to an improved bacterial growth medium composition adapted for growth of bacteria in an aqueous growth medium which comprises a powdered growth medium adapted to be admixed with water including a water soluble alkaline earth metal cation in a compound A admixed with an anion in compound B in an amount sufficient to react in water to form an essentially water insoluble salt, base or mixture thereof, including the alkaline earth metal cation and the anion, wherein the powdered growth medium is adapted to provide an amount of the insoluble salt, base or mixture thereof in the aqueous medium sufficient to neutralize at least some of the acid generated by the acid producing bacteria and wherein the growth medium when admixed with water has an initial pH between about 4 and 8.5 and is non-toxic to the bacteria.

Patent application Ser. No. 52,960, now U.S. Pat. No. 4,282,255 relates to a method and to compositions for growing acid producing bacteria by using an essentially water insoluble or temporarily water insolubilized and thus initially solid form of an acid neutralizing agent in the growth medium to provide a controlled reaction with acid produced by the bacteria without substantially raising the pH of the growth medium. The specific improvement of application Ser. No. 52,960, now U.S. Pat. No. 4,282,255 involves the addition of essentially insoluble magnesium compounds such as trimagnesium phosphate, or other magnesium phosphate salts which are insoluble under neutral and near neutral conditions (pH 6.5-7.5) with acid generating bacterial cultures used as starters in the fermentation industry. As the bacteria grow and acid is produced, the insoluble neutralizing agent is solubilized thereby immediately neutralizing the acids as they are produced. Because of the insoluble nature of the neutralizing agent it has essentially no influence on the soluble composition of the nutrient growth media and sufficient quantities may be added to neutralize all the acid produced during subsequent growth depending on the availability of growth factors on the medium and the nature of the bacteria. Therefore, the bacteria can grow to higher populations and do not suffer from significant acid injury during growth as wound occur without the insoluble neutralizing agent. Consequently, bacteria generated in such media are poised to transform a substrate such as milk at a faster rate and with a minimum lag compared to bacteria produced where the acid is not neutralized.

Trimagnesium phosphate is available commercially on the market from a limited number of suppliers. Industrial processes which depend on extremely limited sources of essential ingredients are commercially untenable. Magnesium ammonium phosphate also is generally unavailable in bulk quantities for industrial use.

The present invention is an improvement over Ser. No. 52,960. The improvement occurs by chemically generating a desired insoluble neutralizing agent by chemical reaction when the ingredients are mixed in water or milk or other suitable liquids to provide a growth medium. Preferably the ingredients are in the form of powders for ease of dispersion in aqueous solution. There is a substantial economic advantage from using the present invention. Inhalation health hazards are reduced in one of the improved methods (Example 1 hereinafter) since dry blending of fine powders of the compounds of magnesium hydroxide or trimagnesium phosphate is not necessary. The importance of this improvement in working conditions is significant.

The present invention thus provides a method for generating an essentially water insoluble, non-toxic neutralizing agent by chemical reaction in a bacterial growth medium. This in situ generation of the insoluble neutralizing agent occurs after addition of water or milk or other suitable liquid which forms the desired insoluble neutralizing agent. The resulting insoluble neutralizing agent is a base or salt or mixture thereof and is adapted to provide a controlled reaction with the acid produced by the bacteria without substantially raising the pH of the growth medium. The neutralizing agent is generated in the growth medium prior to the growth of the bacteria and is present in an amount sufficient to maintain the pH at a level beneficial for bacterial growth.

Liquid bulk starter compositions for growing bacteria in media wherein the insoluble neutralizing agent has been generated in situ can be provided by the present invention. Further, bacterial compositions with enhanced storability and viability because of the essentially insoluble neutralizing agent are produced. Both of these are described in Ser. No. 52,960, now U.S. Pat. No. 4,282,255.

The physical characteristics of the in situ generated insoluble neutralizing agents are in some instances different from neutralizing agents which are not generated in situ. Further in some cases the invention allows use of chemicals which are readily and uniformly blended in commonly, commercially used tumbler bins, whereas neutralizing agents which are not generated in situ are not well adapted for uniform blending in tumbler bins because of density and particle size character. In some instances the invention allows production of powders by spray drying water soluble chemicals which are low in equipment abrasion when compared to spray drying of water insoluble neutralizing agents in suspension which was necessary prior to the invention. The method of in situ generation and the resulting aqueous growth medium are particularly adapted to growing lactic acid producing bacteria which are then used in making food and beverage fermented products for animals and humans.

The principle alkaline earth metal cations of compound A are magnesium and calcium with the former being preferred as described in our co-pending application Ser. No. 52,960, now U.S. Pat. No. 4,282,255. Other alkaline earth metal cations which can be used, particularly in non-food settings, are barium and strontium so long as the resulting salts or bases are non-toxic to the bacteria in the aqueous growth medium.

Compound B preferably includes a phosphate anion since these form insoluble salts with the alkaline earth metal cations and are very effective neutralizing agents. Other compounds B can include various anions such as hydroxide, carbonate and the like, providing the anion reaction product with the alkaline earth metals is essentially insoluble in water.

In general, the reaction of compound A and compound B will involve essentially stoichiometric molar amounts of each although an excess of one or the other can be tolerated depending upon the particular acid producing bacterium that is being grown so long as the reaction products in water are non-toxic to the bacteria. In general, the powdered growth medium compositions contain between about about 5 and 30 weight percent of each of the compounds A and B. It will be appreciated that compounds A and/or B can be toxic to the bacteria at the levels used in the powdered growth medium but that once they react to form the insoluble compound in the aqueous solution for growth of the bacteria this is not a problem. Preferably the compounds A and B are substantially water soluble.

In general, the pH of the growth medium with the insoluble salt or base or mixture thereof is between about 4 and 8.5 in water. Higher or lower pH levels can be used provided the acid producing bacteria are tolerant to the basicity or acidity. The insoluble compounds which are formed in situ in the aqueous growth solution can be alkaline earth metal hydroxides, phosphates, carbonates, citrates and the like. Preferred are magnesium phosphate tribasic, magnesium phosphate dibasic, magnesium orthophosphate, magnesium orthophosphate monohydrogen, magnesium pyrophosphate, calcium phosphate tribasic, calcium phosphate dibasic, calcium phosphate monobasic, calcium carbonate, magnesium carbonate, magnesium hydroxide, magnesium ammonium phosphate, and the like as insoluble compounds. The magnesium phosphates, including magnesium ammonium phosphate, are particularly preferred since these compounds tend to inhibit phage in an aqueous growth medium involving lactic acid producing bacteria which are sensitive to phage. This class of bacteria includes those which are used for producing products like buttermilk, yogurt, cottage cheese and the like.

The compounds A and B are preferably admixed with the other ingredients conventionally used in growth media in dry powdered forms so that the product is a powder. In general, the powdered growth media should be contained in relatively moisture secure packages to prevent premature reaction of the compounds A and B because of atmospheric moisture or accidental contact with water. Various well known moisture proof packs are suitable for this purpose.

The other nutrients used in liquid or powdered growth medium are well known and include an assimilable carbohydrate, a nitrogen source and usually essential minerals where the object is to increase the number of the bacteria. The carbohydrates are usually in the form of simple sugars such as lactose or glucose which are directly metabolized by the bacteria to produce the acids. The nitrogen source preferably includes various forms of yeast such as yeast extract or other sources of assimilable amino acids such as tryptone, casein, phytone, peptone and beef extract. The essential minerals vary from bacteria to bacteria but generally include trace amounts of transition metal salts such as manganese and magnesium salts. In the present invention, the insoluble magnesium salts can function to provide part of the magnesium requirement of the bacteria upon reaction with the acid. Many variations in growth media are described in the prior art and are well known to those skilled in the art.

The phrase "essentially water insoluble" means an insoluble compound as a base or salt which functions as an acid neutralizing agent and which has a solubility in water (having a neutral pH without the agent) at 25° C. of less than about 10 grams per liter. Based upon the definition of the United States Pharmacompea IXI, 1975, compounds are "slightly soluble" at 1.0 grams to 10.0 grams per liter; very "slightly soluble" at 0.1 gram per liter to 1.0 gram per liter and "practically insoluble" or "insoluble" at less than 0.1 gram per liter. The phrases "essentially water insoluble" or "water insoluble" as used herein cover all of these solubilities.

SPECIFIC DESCRIPTION

Examples of the present improvement are set forth hereinafter and it is intended that they be only illustrative. Cultures used in some of the examples are deposited in the collection maintained in the Department of Microbiology, Oregon State University and are freely available without cost to the public.

EXAMPLE 1

Patent application Ser. No. 52,960, filed June 28, 1979, now U.S. Pat. No. 4,282,255 clearly shows the advantage of using the magnesium phosphates in a growth media for growing acid producing bacteria to be used in fermenting foods. However, the magnesium phosphates are expensive and of limited availability commercially. In addition, production of these agents requires expensive equipment not always readily available and further the magnesium phosphates are extremely abrasive compounds and require special handling to avoid excessive equipment wear and damage if these compounds are to be prepared as dry powders for blending with commercial powdered bacterial growth media. The following example of the invention shows the in situ generation of the desired magnesium phosphate in a manner which avoids all the difficulties listed.

A growth medium was prepared by combining 710 pounds of a dry powdered material containing magnesium citrate (compound A), 933 pounds of dibasic ammonium phosphate (compound B), 181 pounds of yeast extract and 1,275 pounds of whey powder. The dry powder material containing magnesium citrate was prepared by adding 583 pounds of anhydrous citric acid to 200 gallons of water followed by 715 pounds of a magnesium hydroxide aqueous slurry containing 58.3% solids, with stirring for 30–60 minutes until the reaction was essentially complete and then by spray drying.

The entire combination of dry powder was then tumble mixed in a bin and later used to grow acid producing bacteria for use in food fermentation. The insoluble salt is essentially magnesium ammonium phosphate.

In growing bacteria the powder was generally mixed in stirring water (50–75 pounds/100 gallons) heated to about 85° C. for 45 minutes, cooled to about 24° C. and inoculated with 1% by weight of a lactic acid producing bacteria (about $1 \times 10^9$ cells per ml) and allowed to ferment for about 12–20 hours. The initial growth medium pH was generally about 6.5–7.1 and the final pH was about 4.9–5.4. When compared to bacteria produced using growth media reported in Example 10 of application Ser. No. 52,960, now U.S. Pat. No. 4,282,255 the bacteria grown using in situ generation of the neutralizing agent described above were essentially equivalent in activity and cell numbers.

The advantages of the above example are numerous. These include: (a) expensive and limited source magnesium ammonium phosphate or other magnesium phosphates need not be used, (b) the ratio of compounds A and B can readily be varied to optimize initial pH, final pH and neutralizing capacity with more flexibility, (c) the soluble or mostly soluble magnesium citrate produced by combining magnesium hydroxide and citric acid can be spray dried with minimal equipment wear and damage, (d) the powders of the medium can be tumble bin blended to produce a uniform product, (e) the physical properties of the powdered product after hydration are such that a minimum of settling or suspending materials occurs during fermentation because of the fine dispersion of the insoluble salt, (f) the heat produced by in situ generation of the neutralizing agents not only does not adversely affect the medium, but can contribute somewhat to energy savings in heating an aqueous medium mixture for bacterial growth, and (g) the heat evolved on addition of magnesium hydroxide to the citric acid solution is substantial and makes a definite contribution to the energy savings by chemically preheating the reaction mixture as is needed prior to spray drying. This is a preferred but an optional step

EXAMPLE 2

A powdered blend mixture was prepared containing about 17.7% trisodium citrate dihydrate and 8.2% magnesium hydroxide (which can react in water to form a magnesium citrate which acts in part as compound A), along with 21.2% ammonium phosphate monobasic and 5.9% ammonium phosphate dibasic (which can act as compound B), 6.0% yeast extract, and 41% whey by mixing the ingredients in a tumbler bin to produce 3,000 pounds of product. After preparation, the powder was added to stirred water (75 pounds/100 gallons), heated to 85° C. for 45 minutes and allowed to cool to about 24° C. prior to inoculation (1%) by weight with a lactic acid producing streptococus starter culture. This medium allows in situ formation of the insoluble salt magnesium ammonium phosphate through reaction after the medium is hydrated. Repeated field trials were conducted with the bacteria grown in this medium and they grew in large numbers and were highly active. It should be noted that the exact chemical reaction sequence and specific chemical composition of the neutralizing agent(s) may be complex.

Physical-chemical characteristics of the neutralizing agent generated in conjunction with other medium ingredients were somewhat different than expected. In a 300–500 gallon starter tank, it was routine to find a dense cement-like mass or the bottom of the tank at the end of the 12–20 hour fermentation period. The mass sometimes had to be chipped out of the tanks with a hammer. This problem was not nearly so prevalent with the medium described in Example 1, even though very similar neutralizing agents were being generated in situ. Extremely vigorous agitation could prevent some of the hard cake formation, but the insoluble residue was still in excess by comparison to Example 1. The step-wise process involved in generating the neutralizing agent in Example 1 is thus preferred.

The trisodium citrate available citrate content of commercial product was extremely variable ranging from 5.8 to 24.5% for a four-fold variation rather than being extremely close to the desired 17.7%. Varying blending times of the dry powders for 10, 20 or 30 minutes did change the result. Thus, variation in final formulation due to variation behavior of the powdered growth medium in the field. This is in contrast to what was observed with the medium of Example 1. In production of the medium by Example 1, there was only a 1.4% citrate variation on a production basis and thus the ingredients were adapted to standard tumbler bin blending.

It should be noted that workmen complained when working with powdered magnesium hydroxide of nosebleeds and eye irritation due to powder aerosolization. There was less problem with Example 1 where the magnesium hydroxide is used as the slurry and not a powder. Also, production of magnesium hydroxide by spray drying the slurry is quite expensive as the abrasive powder wears out the spray nozzle. The magnesium citrate composition produced in Example 1 is less abrasive and the equipment lasts longer.

EXAMPLE 3

A growth medium was prepared by combining 8.3% magnesium hydroxide, and 11.7% anhydrous citric acid (which react in water to form magnesium citrate in the growth medium), 43.1% whey solvents, 31.1% dibasic ammonium phosphate (compound B) and 5.8% yeast extract to produce 3,000 pounds and blended together in a tumbler bin. The product was used to grow bacteria as before (75 pounds/100 gallons of water), wherein magnesium ammonium phosphate is formed in situ. The bacteria produced were excellent as before and the initial pH and final pH were about the same as before. Extensive field testing of the product resulted in a cement-like cake on the bottom of the starter tank for some trials and not for other trials (like Example 2). Also, analysis of citrate concentration of citric acid showed high variations of available citrate on the order of four-fold as observed with trisodium citrate and as shown in Example 2. Thus, the alternate method for in situ generation of neutralizing agent which uses citric acid as in Example 1 rather than trisodium citrate like Example 2, provided a media very similar chemically in compositions to the Examples 1 and 2 but the characteristics were different from Example 1 and similar to Example 2.

If uniform quality citric acid or sodium citrate could be obtained, the results would be more comparable to Example 1. However, magnesium hydroxide may contribute to the cement-like by product.

EXAMPLE 4

Commercial ultra-high temperature short time pasteurization is sometimes accomplished by pumping an aqueous bacterial growth medium through a tightly packed heated plate pasteurizer at temperatures above 200° F. With some media in patent application Ser. No. 52,960, now U.S. Pat. No. 4,282,255 and the media described in Examples 1 to 3 of this application, there is often a buildup of insoluble media ingredients on the pasteurizer plate which results in plugging. However, a medium which consists of two separately pasteurized parts followed by in situ generation of the neutralizing agent works well. For each 100 gallons of starter to be prepared, about 14 pounds of a mixture of magnesium hydroxide (39.9%) and citric acid monohydrate (60.1%, can be added to 41 gallons of water to form magnesium citrate (Compound A) in solution and then pasteurized with a ultra-high temperature short time unit without problems since the solids are mostly dissolved. Then 24 pounds of the mixture of dibasic ammonium phosphate (67.2%), yeast extract (16.6%), and monobasic ammonium phosphate (16.2%) can be added to 56 gallons of suitable aqueous medium such as water containing whey solids or skimmed milk which can be pasteurized with the ultra high temperature short time pasteurizer. The liquid is then mixed into the stirring tank containing the pasteurized magnesium citrate. After combination, the insoluble neutralizing agent magnesium ammonium phosphate is generated in situ and the media is excellent for growing lactic acid producing bacteria.

EXAMPLE 5

A growth medium, No. 1 below, was prepared by mixing 5.5 ml (7.3 grams) of phosphoric acid and 200 ml of tap water followed by 5.2 grams of magnesium hydroxide powder with stirring for 10 minutes. Heat is given off and the temperature rises to 57° C. This forms a magnesium phosphate which has limited solubility in water. Then 500 ml of tap water was added followed by 10.5 grams of dibasic ammonium phosphate, 10.5 grams of trisodium citrate dihydrate, 3.5 grams yeast extract and 24.5 grams whey powder. This medium allowed a chemical reaction to occur in situ to generate a magnesium phosphate and magnesium ammonium phosphate complex by using readily available and inexpensive starting materials rather than using an expensive and limited availability material., e.g., magnesium phosphate and magnesium ammonium phosphate. For comparison, another growth medium, No. 2 below, as in Ser. No. 52,960, now U.S. Pat. No. 4,282,255 Example 10, was also prepared by blending together the dry powder 10.5 grams magnesium phosphate tribasic, 10.5 grams dibasic ammonium phosphate, 10.5 grams trisodium citrate dihydrate, 3.5 grams yeast extract and 24.5 grams whey powder, followed by addition to 700 ml of water. Both preparations were continuously stirred, heated to 85° C. within 20 minutes, maintained at 85° C. for 45 minutes and cooled to 24° C. and inoculated in successive trials with commercially available streptococcal lactic acid producing bacteria. Also evaluated as a control was a growth medium (No. 3 below) containing 11% non-fat dry milk solids and 700 ml of tap water, heated and cooled and innoculated as stated above. The pH time course of media were as shown in Table I:

TABLE I

| Elasped Time In Hours | Recorded pH of the Media | | | | | | | |
|---|---|---|---|---|---|---|---|---|
| | Culture DPL102 | | | Culture DPL104 | | | Culture HAN72 | |
| | 1 | 2 | 3 | 1 | 2 | 3 | 1 | 3 |
| 0 | 7.00 | 6.92 | 6.46 | 6.84 | 6.44 | 6.41 | 7.01 | 6.46 |
| 13 | 5.12 | 5.06 | 4.59 | 5.50 | 5.17 | 4.99 | 5.28 | 4.80 |
| 14 | 5.11 | 5.10 | 4.56 | 5.34 | 5.08 | 4.78 | 5.28 | 4.82 |
| 15 | 5.11 | 4.98 | 4.57 | 5.33 | 5.64 | 4.70 | 5.28 | 4.81 |
| 16 | 5.09 | 4.95 | 4.57 | 5.32 | 5.04 | 4.66 | 5.28 | 4.82 |

The medium 1, which contains an in situ generated neutralizing agent and is much less expensive to prepare than medium 2, is equally effective in maintaining the growth medium pH in a range which is known to be conducive to growth of healthy active cells while the pH falls too low in the non-fat milk control medium (medium 3).

Activity tests of bacteria grown in the above media 1 and 3 were also conducted by innoculating culture HAN72 (1%) into non-fat dry milk (11% by weight solids) and measuring the pH for four hours and six hours post inoculation for freshly grown cells and for cells maintained in the refrigerator for eight days. The four and six hour pH values were: 5.69 and 4.98 (cells from medium 1) vs. 6.07 and 5.50 (cells from medium 3) for fresh cells and 5.78 and 5.02 vs. 6.12 and 5.47 for eight day old cells, respectively. It is clear that cells grown in medium 1 are more active initially and after storage than cells grown in medium 3. Better acid control was achieved with medium 1 as compared to medium 2.

Either the mono or dibasic ammonium phosphate can serve as a source of ammonium phosphate anion. The diammonium phosphate is believed to react first.

As can be seen, the in situ method of generating the neutralizing agent is very effective.

We claim:

1. In the method for growing acid producing bacteria in an aqueous growth medium including bacterial nutrients, particularly a carbohydrate, a nitrogen source and essential minerals, the improvement which comprises:
   providing a compound A, which compound is a dry, water soluble magnesium compound; and
   reacting in water containing the bacterial nutrients and prior to addition of the bacteria, a magnesium cation from compound A with an anion from a compound B which reacts with the magnesium cation to form, by a reaction in situ, an aqueous medium containing an essentially water insoluble reaction product that (a) is a salt, base or mixture thereof, (b) includes the magnesium cation and the anion, and (c) is acid neutralizing in the medium, wherein the resulting medium includes an amount of the insoluble reaction product sufficient to neutralize at least some of the acid generated by acid producing bacteria grown in the medium and wherein the resulting medium is nontoxic to the bacteria.

2. The method of claim 1 wherein compound B includes a phosphate anion and wherein compound A and compound B are provided and added to the water as a dry mixture.

3. The method of claim 1 wherein compound B is an ammonium phosphate, and the insoluble salt formed is essentially magnesium ammonium phosphate.

4. In the method for growing acid producing bacteria in an aqueous growth medium including bacterial nutrients, particularly a carbohydrate, a nitrogen source and essential minerals, the improvement which comprises:
   providing dry magnesium citrate by reacting magnesium hydroxide with citric acid in an aqueous solution and drying the resulting magnesium citrate to a powder; and
   reacting in water containing the bacterial nutrients and prior to addition of the bacteria, a magnesium cation from the dry magnesium citrate with an anion in a compound which reacts with the magnesium cation to form, by a reaction in situ, an aqueous medium containing an essentially water insoluble reaction product that (a) is a salt, base or mixture thereof, (b) includes the magnesium cation and the anion, and (c) is acid neutralizing in the medium, wherein the resulting medium includes an amount of the insoluble reaction product sufficient to neutralize at least some of the acid generated by acid producing bacteria grown in the medium and wherein the resulting medium is nontoxic to the bacteria.

5. A dry composition for admixture with water to form a neutralizing system that is useful for pH maintenance in a bacterial growth medium for acid-producing bacteria, said composition comprising at least two different salt materials including:
   (a) a first salt material that is soluble in water and that provides in solution a magnesium cation; and
   (b) a second salt material that provides at least one anion that can react in solution with a magnesium cation of said first salt material, to form an essentially insoluble reaction product;
   said insoluble reaction product being capable of reacting with acid to neutralize the acid, and thus being capable of reaction with acid generated in a growth medium, in which said composition is present, by acid-forming bacteria, to neutralize the acid and thus function as a pH stabilizer during a growth phase of the bacteria.

6. A composition according to claim 5 wherein, in said second salt material, said anion is selected from the group consisting of hydroxides, phosphates, carbonates, and mixtures thereof.

7. A composition according to claim 5 wherein said composition also comprises, as bacterial nutrients, a source of assimilable carbohydrate and a nitrogen source.

8. A suspension of the composition of claim 7 that is useful as a growth medium for acid-producing bacteria and that is not toxic to said bacteria.

9. A dry powder composition for admixture with water to form a neutralizing system that is useful for pH maintenance in a bacterial growth medium for acid-producing bacteria, said composition comprising:
   bacterial nutrients, including a source of assimilable carbohydrate and a nitrogen source; and
   at least two different salt materials including
      (a) magnesium citrate that provides in solution magnesium cations and citrate anions; and
      (b) dibasic ammonium phosphate that provides in solution ammonium cations and phosphate anions, which phosphate anions can react in solution with the magnesium cations of said magnesium citrate, to form a magnesium phosphate reaction product in said aqueous medium;
   said insoluble reaction product being capable of reacting with acid to neutralize the acid, and thus being capable of reaction with acid generated in a growth medium, in which said composition is present, by acid-forming bacteria, to neutralize the acid and thus function as a pH stabilizer during a growth phase of the bacteria.

10. A dry composition for admixture with water to form a neutralizing system that is useful for pH maintenance in a bacterial growth medium for acid-producing bacteria, said composition comprising at least two different salt materials including:
    (a) a first salt material that is soluble in water and that provides in solution magnesium cations; and
    (b) a second salt material, which material provides in solution phosphate anions that can react in solution with the magnesium cations of said first salt material, to form a reaction product that is essentially insoluble in water;

said insoluble reaction product being capable of reacting with acid to neutralize the acid, and thus being capable of reaction with said generated in a growth medium, in which said composition is present, by acid-forming bacteria, to neutralize the acid and thus function as a pH stabilizer during a growth phase of the bacteria.

11. A composition according to claim 10 wherein said composition also comprises, as bacterial nutrients, a source of assimilable carbohydrate and a nitrogen source.

12. An aqueous suspensions of the composition of claim 11 that is useful as a growth medium for acid-producing bacteria and that is not toxic to said bacteria.

13. A composition according to claim 5 wherein the first salt material provides in solution a citrate anion.

14. A composition according to claim 10 wherein the first salt material provides in solution a citrate anion.

* * * * *

UNITED STATES PATENT AND TRADEMARK OFFICE
CERTIFICATE OF CORRECTION

PATENT NO. : 4,615,978
DATED : October 7, 1986
INVENTOR(S) : WILLIAM E. SANDINE and JAMES W. AYRES It is certified that error appears in the above—identified patent and that said Letters Patent is hereby corrected as shown below:

In the Specification:

Column 6, line 60, "or" should be --on--.

Column 7, line 9, after "variation", insert --associated with the ingredients was responsible for variable".

In the Claims:

Column 11, line 5, "said" should be --acid--.

Column 12, line 3, "suspensions" should be --suspension--.

Signed and Sealed this

Twenty-ninth Day of December, 1987

Attest:

DONALD J. QUIGG

Attesting Officer

Commissioner of Patents and Trademarks